United States Patent [19]

Mogos et al.

[11] 3,970,074
[45] July 20, 1976

[54] METHOD OF AND APPARATUS FOR MAKING MEDICAL THERMOGRAPHS

[75] Inventors: Ion Mogos; Cornel Ionescu; Dionisie Angelescu; Nicolae Dumitrescu; Millo Andreescu; Constantin Neascu; Mircea Brozici; Mihai Birzanescu; Alexandru Puie; Gheorghe Vasilica, all of Bucharest, Romania

[73] Assignee: Spitalul Clinic Filantropia Bucuresti, Bucharest, Romania

[22] Filed: Aug. 22, 1974

[21] Appl. No.: 499,408

[52] U.S. Cl. .................................. 128/2 H; 73/342; 73/343.5
[51] Int. Cl.² ...................... A61B 5/00; G01K 7/24
[58] Field of Search ............. 128/2 H, 2 A, 2.05 R, 128/2.06 E, DIG. 4; 73/342, 343.5, 341

[56] References Cited
UNITED STATES PATENTS

| | | | |
|---|---|---|---|
| 3,294,084 | 12/1966 | Schuler et al. | 128/DIG. 4 UX |
| 3,387,608 | 6/1968 | Figar | 128/2.06 E |
| 3,525,330 | 8/1970 | Greene | 128/2.06 E |
| 3,534,727 | 10/1970 | Roman | 128/DIG. 4 UX |
| 3,699,813 | 10/1972 | Lamb | 128/2 H X |

FOREIGN PATENTS OR APPLICATIONS

| | | | |
|---|---|---|---|
| 274,612 | 7/1951 | Switzerland | 128/DIG. 4 |

OTHER PUBLICATIONS

Bio–Med. Engineering, (Aug. 1971), vol. 6, No. 8, pp. 358–362.
Howell Instrument, Inc. Catalogue, BH-103, Digital Data System, 6 pages, rec'd June 3, 1966.

*Primary Examiner*—Kyle L. Howell
*Attorney, Agent, or Firm*—Karl F. Ross; Herbert Dubno

[57] ABSTRACT

An array of thermistors mounted on a resilient sponge are pressed against a body area to be examined such that each thermistor contacts a respective location on the body area. The outputs of the thermistors are fed to an electronic recording device (digital voltage recorder) which enters them on a chart so as to produce a visual representation illustrating the variations in temperature on the body area being examined.

6 Claims, 7 Drawing Figures

3,970,074

METHOD OF AND APPARATUS FOR MAKING MEDICAL THERMOGRAPHS

FIELD OF THE INVENTION

The present invention relates to a method of and an apparatus for producing a medical thermograph. More particularly this invention concerns a medical thermographic system for detecting and measuring thermogenic sites on the human body.

BACKGROUND OF THE INVENTION

It is known that various medical conditions or pathologies are characterized by the generation of heat. Such is, for instance, the case with a tumor or a cyst whose site is at a temperature substantially above the average skin temperature.

The traditional method of obtaining a medical thermograph has been simply to juxtapose a heat-sensitive film with the body area in question, thereby obtaining upon development a picture showing the temperature variations in the region.

In yet another system infrared radiation emitted by the region in question is registered on film or picked up by a television-type camera so as to give a visual representation of the region showing the temperature variation.

All of these systems have substantial disadvantages. First of all it is almost impossible to obtain an accuracy of greater than 0.1°C, and with many systems it is impossible to obtain a precision of greater than 1°C.

In addition the known medical thermographic arrangements are extremely expensive and give results which are only nominally usable, a classic example is that a local region having a high blood vessel density is frequently recorded as if it were a tumor or the like, so that subsequent examination is necessary to obtain a meaningful diagnosis.

The principal disadvantage of all of the prior-arts thermographic systems is that they cannot be effectively analyzed, since the information is generally in the form of various black and white or color intensities, even with an optical densitometer. An expert is required to study the thermograph and give a subjective analysis thereof. There is no possibility of categorizing and objectively measuring the information obtained.

OBJECTS OF THE INVENTION

It is therefore an object of the present invention to provide an improved medical thermographic method and apparatus.

Yet another object is the provision of such an apparatus whose output can be objectively analyzed and, indeed, reduced to measurable data.

A further object is the provision of a medical thermographic system which is extremely sensitive and easy to use by even relatively unskilled medical personnel.

SUMMARY OF THE INVENTION

These objects are attained according to the present invention in a system wherein an array of temperature sensors is juxtaposed with the body region to be scanned. Each of these sensors gives an output corresponding to the temperature of the respective body region. These outputs are compared in an electronic output device which produces a thermograph that corresponds to the body region being scanned.

Such a system has the considerable advantage that it subdivides the region of interest into a multiplicity of discrete areas whose respective temperatures are measured and then entered in a corresponding visual representation of the region. The electronic output device may in accordance with this invention produce a simple printed graph either resembling a weather map with isotherms connecting points of like temperature, or wherein colors are used, such as red to indicate regions above normal temperature and blue to indicate regions below normal temperature. It is possible with such a system to obtain extremely precise results using solid-state temperature sensors which are capable of detecting temperature variations substantially smaller than 0.1°C. Thus it is possible to produce a thermograph which is very precise and which can be used to pinpoint the thermogenic sites.

A particular advantage of the present invention lies in the ability with which the output can be reduced to storable and analyzable data, particularly for a computer or the like. Indeed the data so obtained can be analyzed statistically. Such an arrangement is readily adapted for locating tumors, diagnosing other ailments such as rheumatism or simple vascular and inflammatory diseases, studying various endocrine systems, and even localizing and studying a foetus while still in the womb. In addition the storability and reducability of the information so obtained allows the day-by-day comparison of the thermograph for a patient under treatment so as to determine the effectiveness of the therapy.

According to the present invention, a numerical recorder is provided which is operated at a rate of displacement of the sensing sponge over the body to provide numerical temperature readings, as detected by a digital voltmeter so that a precise numerical indication of temperature can be provided at each point. For monitoring the temperature at selected locations over a period of time, we may make use of an analog recorder which registers the data. The data thus measures at different points of the human body the superficial temperature by means of thermistors connected in bridge circuits connected to a numerical display voltmeter to provide a higher precision of the determination of the measured temperature values.

BRIEF DESCRIPTION OF THE DRAWING

The above and other objects, features, and advantages of the invention will become more readily apparent from the following description, reference being made to the accompanying drawing in which.

SPECIFIC DESCRIPTION

Figure 1:
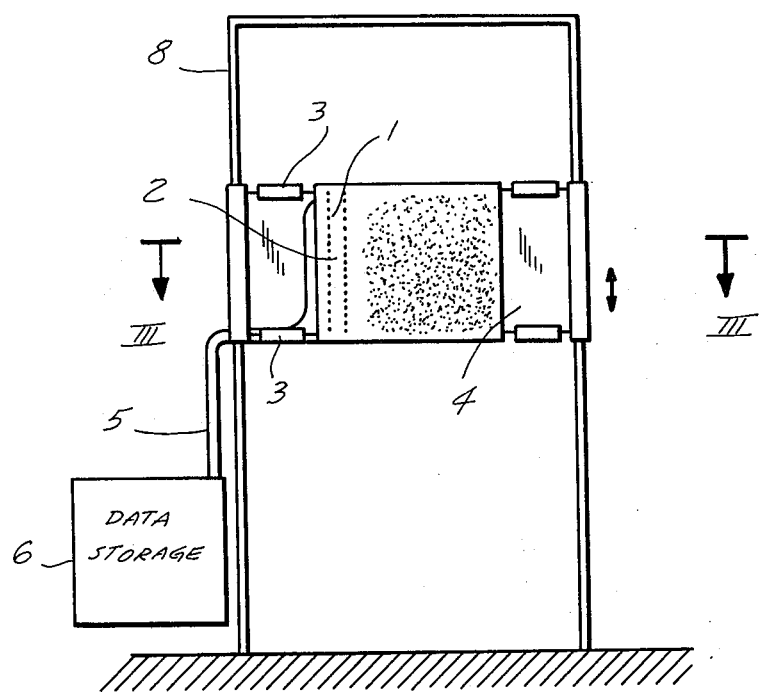
FIG. 1 is a side view of an apparatus in accordance with the present invention.
Figure 3:
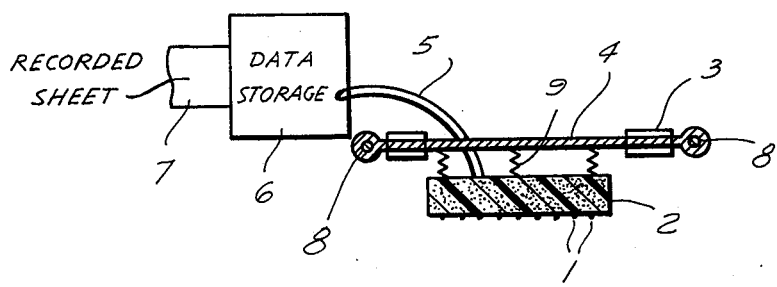
FIG. 3 is a section taken along line III—III of FIG. 1.

As is shown in FIGS. 1 and 3 a support 4 is vertically displaceable on upright rods 8 and can be clamped to these rods 8 by means of securing devices 3. A large sponge 2 is supported by means of springs 9 on the support 4 and carries an array of thermistors 1 which are connected via a multiconductor cable 5 to a data storer and printer 6 that produces a thermographic recording 7. The portion of the body to be thermographed is pressed against the sponge 2 so that the array of thermistors 1 measures the temperature of the body over a substantial region thereof. The readings so obtained are then printed out as shown at 7 to give a permanent record.

Figure 2:
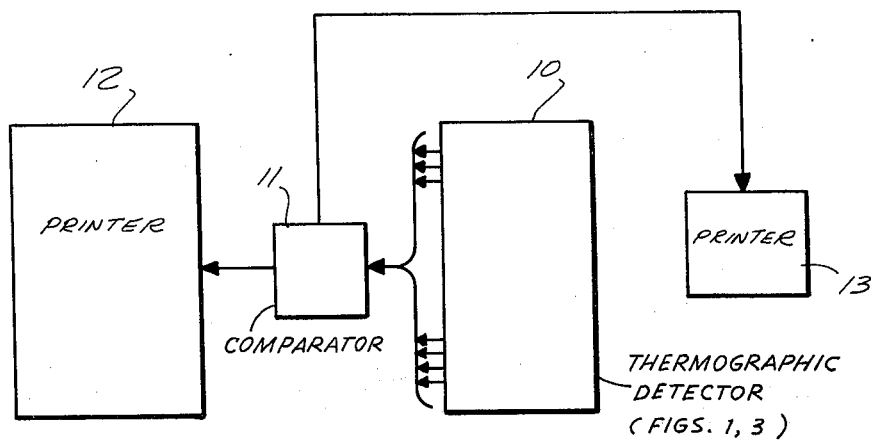
FIG. 2 is a schematic block diagram of the system of this invention.

It is also possible as shown in FIG. 2 to connect the many outputs of a thermographic device 10 somewhat as described above to a comparator 11 which feeds the information to a printer 12 and to a secondary printer 13 which responds to only wide variations from a median temperature. As a general rule a serious pathology is associated with a rather marked temperature difference in the afflicted area.

Figure 4:
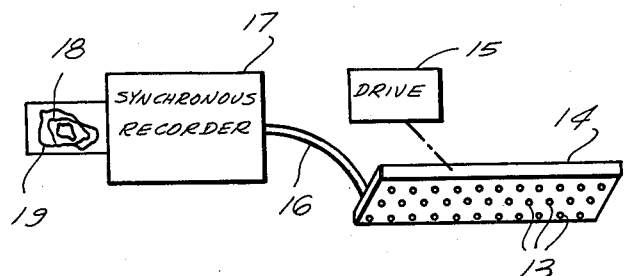
FIG. 4 is a largely diagrammatic view of another system in accordance with this invention.

It is also possible as shown in FIG. 4 to set a group of thermistors 14 in three rows so that each thermistor 13 is about 1 cm from each of its neighbors. A support 14 carrying these thermistors 13 is displaceable by means of a drive 15 and a cable 16 connects the output of the thermistors 13 to a synchronous recorder 17 that reduces the data so obtained to a diagram shown at 18 on which above-average temperatures are marked in red and areas with below average temperatures are marked in blue as shown at 19. Regions of like temperatures are connected together with isotherms.

Figures 5, 6:
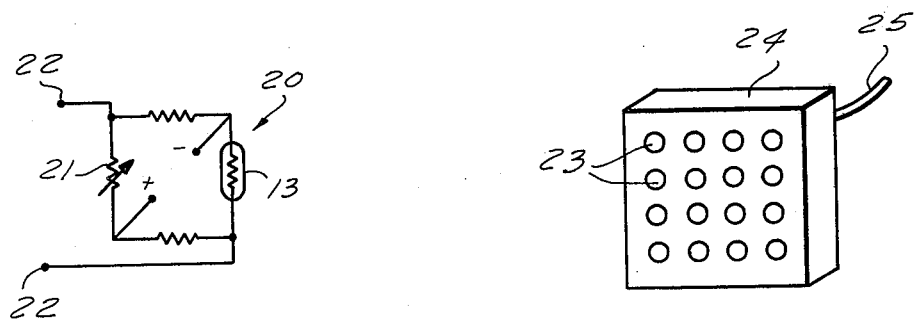
FIG. 5 is a schematic view of a detail of FIG. 4.
FIG. 6 is a perspective view of another apparatus according to this invention.

As is shown in FIG. 5 each of the thermistors 13 is connected in a Wheatstone bridge 20 across from a precision potientiometer 21, the output to the computer or the voltmeters being taken at 22.

As is shown in FIG. 6 a plurality of disk like thermistors 23 may be set in a lucite block 24 which is connected via a flexible cable 25 to a recording device. Such an arrangement can be hand held and pressed against a subject area in order to produce a small thermograph. The thermograph so produced can be readily used for locating the exact point at which a biopsy should be taken.

The transducers used for temperature measurement have a sensitivity of greater than 0.01°C so it is possible to obtain extremely accurate results. The Wheatstone bridge circuit of FIG. 5 is set such that at a temperature of 33°C the resistance of the thermistor 13 is 2400 ohms, allowing the output taken at the 22 to be readily reduced to usable information or fed to a voltmeter for direct reading. This arrangement is stabilized between 27°C and 37°C.

Figure 7:
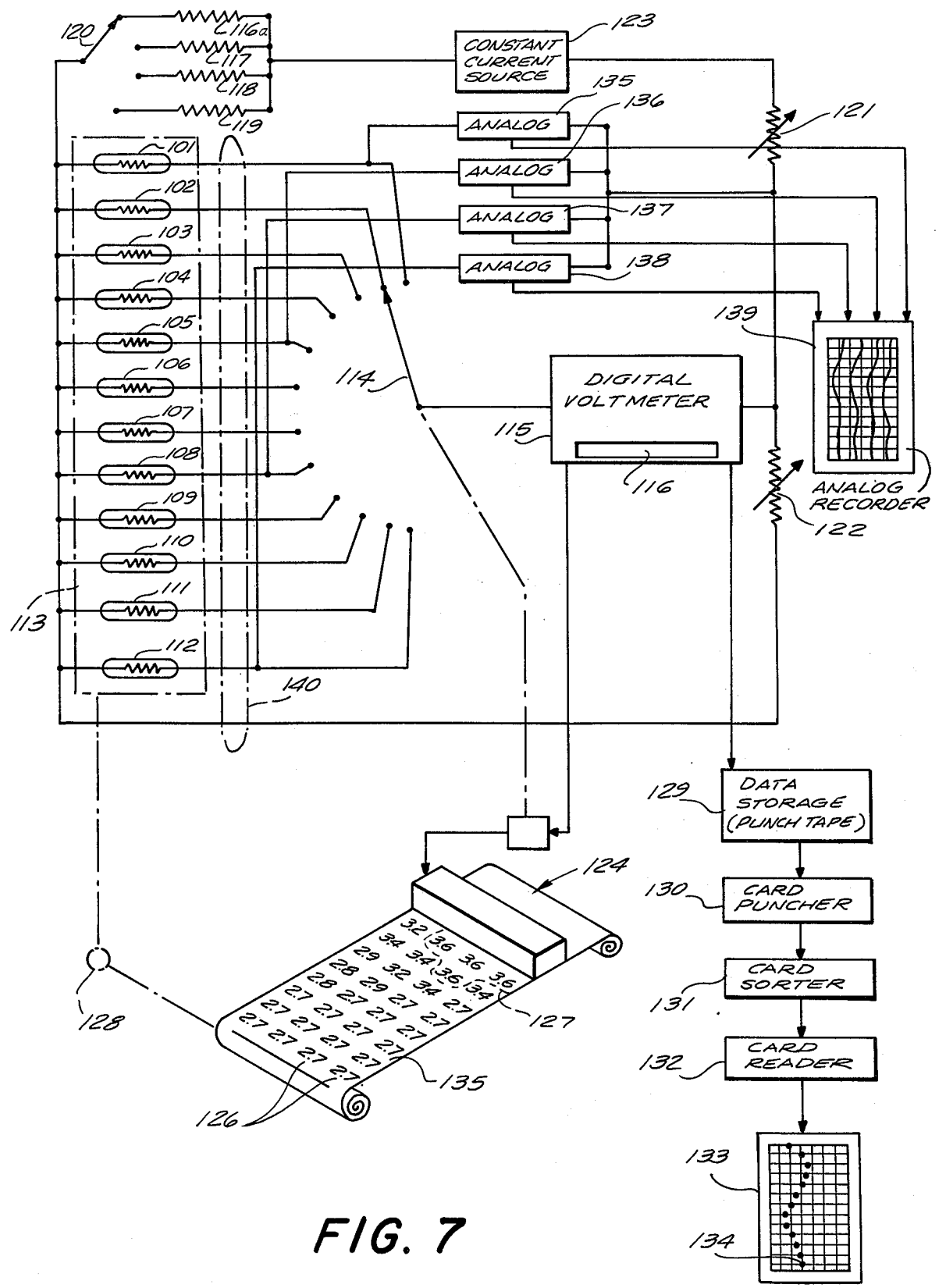
FIG. 7 is a partly schematic and partly block diagrammatic view of an apparatus for carrying out the thermographic measurements according to the present invention.

In FIG. 7, we have shown a system, according to the invention, which comprises a multiplicity of thermistors 101 – 112 which can be considered to be arranged in four vertical rows spaced-apart by about 1 cm on a sponge 113 which is urged by springs, as previously described, against the portion of the body to be scanned. Each of the thermistors 101 – 112 may be selectively connected via a commutating switch 114 to a digital voltmeter 115 which provides at its register 116 a numerical reading of the detected temperature in °C to an accuracy of 0.01°C.

The thermistors are consecutively connected by the switch 114 in a bridge circuit with a decadic set of range resistors 116a, 117, 118 and 119, selected by a range switch 120. A pair of adjustable resistors 121 and 122 form other arms of the bridge which is energized by a constant-current source 123.

The output of the digital voltmeter 115 is applied to a multipoint recorder 124 whose printing head is stepped from point to point in accordance with the position of the switch 114 and which thus prepares on a paper chart 125 a plot of points 126 with the temperatures printed next to each point.

When the temperature is below a critical value, i.e. normal body temperature, the printing may be in blue while temperature readings above the critical value may be printed in red. This permits isobars 127 to be drawn on the charts. The chart 125 is displaced by a motor 128 synchronously with the sponge 113 so that each location on the chart corresponds to a predetermined location on the body.

The output of the digital voltmeter can be applied to a digital memory or storage device represented at 129 as a punched tape which can operate a card puncher 130. When it is desired to analyze the thermograph at a certain location over a period of time, the punched cards may be segregated as to location by a card sorter 132 and then scanned by a card reader which works into a recorder 133 providing a graph of temperature points 134 with time.

Where the change in temperature must be measured continuously over a selected portion of the body, each of the rows of thermistors 101 – 112 may be connected to an analog voltmeter 135, 136, 137 or 138 whose output is fed to a respective channel of a recorder 139 which graphs the temperature as a function of time. A flexible multiconductor cable 140 connects the thermistors with the recording and data-processing system.

In accordance with the present invention it is possible to obtain a highly informative thermograph which gives precise information as to temperature over a given area of the patient's body. Such information has numerous medical uses as described above and can make diagnosis of numerous ailments considerably easier.

In the system of FIG. 7 as described, moreover, the analog recording system can be used with a head consisting of a small number of thermistors, e.g. 12, mounted in a rigid plate whereby the temperature at each point is registered by the analog recorder or the digital recorder as a function of time. For the scanning of the body originally, however, a drive of the recorders in synchronism with a sponge head having, say, 120 sensors is desired.

The system has been found to be particularly suitable in research into metabolic dynamics and local biorhythm, in the study of immune reactions and the pathology of transplants (e.g. the rejection of grafts), permits diagnosis and monitoring of endocrine conditions, allows the localization of tumors and determination of metastases and the determination of the location of the placenta of a pregnant patient.

We claim:

1. A method of thermographically monitoring the body of a human subject comprising the steps of displacing over the skin of the subject an array of thermistors and generating outputs representing the temperature at the body sites adjacent said thermistors; measuring said outputs with a digital voltmeter; numerically recording the temperatures as determined by said digital voltmeter as a function of the position of the respective thermistor on the subject upon a common sheet;

and connecting equal temperature recordals on said sheet to form isotherms mapping the monitored portion of the body of the subject.

2. An apparatus for making a thermograph of the body of a human subject, comprising a sensing head including a support and an array of thermistors mounted on said support and adapted to be applied to the skin of the body of said subject; means forming at least one bridge circuit with each of said thermistors for generating an output voltage representing the temperature of said body at the respective thermistor; a digital voltmeter means connected to said bridge circuit for translating said output voltage into temperature readings; and numerical recorder means connected to said digital voltmeter means for forming a numerical record of the temperatures at sites of said body adjacent said thermistors by recording upon a common sheet said temperatures as a function of the position of the respective thermistor relative to said subject, thereby permitting equal temperature recordals on said sheet to be connected by isotherms mapping the monitored portion of the body of the subject.

3. The apparatus defined in claim 2 wherein said support is a sponge, further comprising means for displacing said sponge over the body of said subject and means for synchronizing said record with the displacement of said sponge.

4. The apparatus defined in claim 3, further comprising analog output means connected to at least one of said thermistors for monitoring the temperature at the corresponding site of said body with time.

5. The apparatus defined in claim 4, further comprising a multiconductor cable connecting said head with said circuit.

6. The apparatus defined in claim 5, further comprising data-storage means connected to said voltmeter for recording the temperatures at a given time and body site upon a punched card.

* * * * *